(12) United States Patent
Khandkar et al.

(10) Patent No.: US 7,780,738 B2
(45) Date of Patent: *Aug. 24, 2010

(54) POLYMER-CERAMIC ARTICULATION

(75) Inventors: Ashok C. Khandkar, Salt Lake City, UT (US); Aaron A. Hofmann, Salt Lake City, UT (US); Ramaswamy Lakshminarayanan, Salt Lake City, UT (US)

(73) Assignee: Amedica Corporation, Salt Lake City, UT (US)

( * ) Notice: Subject to any disclaimer, the term of this patent is extended or adjusted under 35 U.S.C. 154(b) by 1086 days.

This patent is subject to a terminal disclaimer.

(21) Appl. No.: 11/020,424

(22) Filed: Dec. 21, 2004

(65) Prior Publication Data

US 2005/0107888 A1 May 19, 2005

Related U.S. Application Data

(63) Continuation-in-part of application No. 10/171,376, filed on Jun. 13, 2002, now Pat. No. 6,881,229.

(60) Provisional application No. 60/298,669, filed on Jun. 14, 2001.

(51) Int. Cl.
*A61F 2/42* (2006.01)
(52) U.S. Cl. .................................................. 623/22.15
(58) Field of Classification Search .............. 623/22.11, 623/22.17, 22.21, 22.24, 22.28, 22.32, 22.38
See application file for complete search history.

(56) References Cited

U.S. PATENT DOCUMENTS 3,867,728 A 2/1975 Stubstad et al.

4,072,532 A 2/1978 Fletcher et al.

(Continued)

FOREIGN PATENT DOCUMENTS

EP 0821922 2/1998

(Continued)

OTHER PUBLICATIONS

International Search Report for PCT/US02/13654, Sep. 11, 2002, 2 pgs.

(Continued)

*Primary Examiner*—David Isabella
*Assistant Examiner*—Jonathan Stroud
(74) *Attorney, Agent, or Firm*—Mintz, Levin, Cohn, Ferris, Glovsky & Popeo P.C.

(57) ABSTRACT

A ceramic-metal composite articulation is provided with substantial elimination of wear debris, wherein a ceramic material is provided with superior mechanical properties tailored for articulating with ceramic articulations having high flexural strength (greater than about 700 MPa), high fracture toughness (greater than about 7 MPam$^{1/2}$) and a high Weibull modulus (greater than about 20), in comparison with presently available bio-ceramics such as alumina or zirconia. The mechanical property enhancement enables ceramic materials with greater reliability and significantly reduced in-vivo fracture risk to be obtained. Preliminary in-vitro wear performance, to several million cycles using established test protocols, of head/cup components in a prosthetic hip joint made from these ceramics also demonstrates the ultra low wear characteristics. These material properties substantially eliminate polyethylene (PE) wear debris mediated implant failures by offering an optimal combination of bio-mechanical safety and reliability with ultra low wear performance.

8 Claims, 2 Drawing Sheets

U.S. PATENT DOCUMENTS

| | | | |
|---|---|---|---|
| 4,327,449 A | 5/1982 | Charnley | |
| 4,695,282 A | 9/1987 | Forte et al. | |
| 4,743,256 A | 5/1988 | Brantigan | |
| 4,759,766 A | 7/1988 | Buettner-Janz et al. | |
| 5,098,449 A * | 3/1992 | Hwang et al. | 51/307 |
| 5,152,791 A | 10/1992 | Hakamatsuka et al. | |
| 5,158,726 A | 10/1992 | Saita et al. | |
| 5,310,408 A | 5/1994 | Schryver et al. | |
| 5,314,477 A | 5/1994 | Marnay | |
| 5,330,533 A | 7/1994 | Walker | |
| 5,401,269 A | 3/1995 | Buttner-Janz et al. | |
| 5,425,772 A | 6/1995 | Brantigan | |
| 5,462,563 A | 10/1995 | Shearer et al. | |
| 5,464,440 A | 11/1995 | Johansson | |
| 5,525,557 A | 6/1996 | Pujari et al. | |
| 5,534,001 A | 7/1996 | Schlapfer et al. | |
| 5,549,704 A | 8/1996 | Sutter | |
| 5,556,815 A | 9/1996 | Boberski | |
| 5,609,635 A | 3/1997 | Michelson | |
| 5,641,323 A | 6/1997 | Caldarise | |
| 5,697,980 A | 12/1997 | Otani et al. | |
| 5,702,449 A | 12/1997 | McKay | |
| 5,702,453 A | 12/1997 | Rabbe et al. | |
| 5,702,458 A | 12/1997 | Burstein et al. | |
| 5,782,832 A | 7/1998 | Larsen et al. | |
| 5,785,710 A | 7/1998 | Michelson | |
| 5,824,100 A | 10/1998 | Kester et al. | |
| 5,826,586 A | 10/1998 | Mishra et al. | |
| 5,871,546 A | 2/1999 | Colleran et al. | |
| 5,871,547 A * | 2/1999 | Abouaf et al. | 623/22.15 |
| 5,879,404 A | 3/1999 | Bateman et al. | |
| 5,879,407 A | 3/1999 | Waggener | |
| 5,888,222 A | 3/1999 | Coates et al. | |
| 5,888,223 A | 3/1999 | Bray | |
| 5,888,226 A | 3/1999 | Rogozinski | |
| 5,899,939 A | 5/1999 | Boyce et al. | |
| 5,904,720 A | 5/1999 | Farrar et al. | |
| 5,908,796 A | 6/1999 | Pujari et al. | |
| 6,013,591 A | 1/2000 | Ying et al. | |
| 6,033,438 A | 3/2000 | Bianchi et al. | |
| 6,037,519 A | 3/2000 | McKay | |
| 6,039,762 A | 3/2000 | McKay | |
| 6,039,763 A | 3/2000 | Shelokov | |
| 6,069,295 A | 5/2000 | Leitao | |
| 6,086,588 A | 7/2000 | Ameil et al. | |
| 6,090,144 A | 7/2000 | Letot et al. | |
| 6,110,205 A | 8/2000 | Nies | |
| 6,113,637 A | 9/2000 | Gill et al. | |
| 6,113,638 A | 9/2000 | Williams et al. | |
| 6,123,729 A | 9/2000 | Insall et al. | |
| 6,133,180 A | 10/2000 | Miyake et al. | |
| 6,136,029 A | 10/2000 | Johnson et al. | |
| 6,136,369 A | 10/2000 | Leitao et al. | |
| 6,139,585 A | 10/2000 | Li | |
| 6,143,032 A | 11/2000 | Schafer et al. | |
| 6,149,686 A | 11/2000 | Kuslich et al. | |
| 6,149,688 A | 11/2000 | Brosnahan et al. | |
| 6,152,960 A | 11/2000 | Pappas | |
| 6,156,069 A | 12/2000 | Amstutz | |
| 6,179,874 B1 | 1/2001 | Cauthen | |
| 6,187,701 B1 | 2/2001 | Sekino et al. | |
| 6,210,612 B1 | 4/2001 | Pickrell et al. | |
| 6,235,665 B1 | 5/2001 | Pickrell et al. | |
| 6,245,108 B1 | 6/2001 | Biscup | |
| 6,261,322 B1 * | 7/2001 | Despres et al. | 623/23.53 |
| 6,261,586 B1 | 7/2001 | McKay | |
| 6,277,149 B1 | 8/2001 | Boyle et al. | |
| 6,281,264 B1 | 8/2001 | Salovey et al. | |
| 6,296,667 B1 | 10/2001 | Johnson et al. | |
| 6,302,913 B1 | 10/2001 | Ripamonti et al. | |
| 6,322,895 B1 | 11/2001 | Canham | |
| 6,344,061 B1 | 2/2002 | Leitao et al. | |
| 6,346,123 B1 | 2/2002 | McKay | |
| 6,368,350 B1 | 4/2002 | Erickson et al. | |
| 6,371,988 B1 | 4/2002 | Pafford et al. | |
| 6,376,573 B1 | 4/2002 | White et al. | |
| 6,398,811 B1 | 6/2002 | McKay | |
| 6,436,137 B2 | 8/2002 | Wang et al. | |
| 6,447,547 B1 | 9/2002 | Michelson | |
| 6,478,823 B1 | 11/2002 | Michelson | |
| 6,494,883 B1 | 12/2002 | Ferree | |
| 6,494,915 B1 | 12/2002 | Villar Gonzalez et al. | |
| 6,494,917 B1 | 12/2002 | McKellop et al. | |
| 6,511,510 B1 | 1/2003 | de Brujin et al. | |
| 6,517,580 B1 | 2/2003 | Ramadan et al. | |
| 6,527,810 B2 | 3/2003 | Johnson et al. | |
| 6,540,785 B1 | 4/2003 | Gill et al. | |
| 6,540,787 B2 | 4/2003 | Biegun et al. | |
| 6,551,995 B1 | 4/2003 | Opperman et al. | |
| 6,554,867 B1 | 4/2003 | Joos | |
| 6,569,201 B2 | 5/2003 | Moumene et al. | |
| 6,587,788 B1 | 7/2003 | Green | |
| 6,610,097 B2 | 8/2003 | Serbousek et al. | |
| 6,613,091 B1 | 9/2003 | Zdeblick et al. | |
| 6,641,617 B1 | 11/2003 | Merrill et al. | |
| 6,673,075 B2 | 1/2004 | Santilli | |
| 6,676,703 B2 | 1/2004 | Biscup | |
| 6,706,068 B2 | 3/2004 | Ferree | |
| 6,719,794 B2 | 4/2004 | Gerber et al. | |
| 6,723,097 B2 | 4/2004 | Fraser et al. | |
| 6,736,849 B2 | 5/2004 | Li et al. | |
| 6,740,118 B2 | 5/2004 | Eisermann et al. | |
| 6,743,256 B2 | 6/2004 | Mason | |
| 6,758,849 B1 | 7/2004 | Michelson | |
| 6,790,233 B2 | 9/2004 | Brodke et al. | |
| 6,818,020 B2 | 11/2004 | Sun et al. | |
| 6,827,740 B1 | 12/2004 | Michelson | |
| 6,846,327 B2 | 1/2005 | Khandkar et al. | |
| 6,881,229 B2 | 4/2005 | Khandkar et al. | |
| 6,908,484 B2 | 6/2005 | Zubok et al. | |
| 6,972,037 B2 | 12/2005 | Zubok et al. | |
| 6,972,038 B2 | 12/2005 | Zubok et al. | |
| 6,989,030 B1 | 1/2006 | Ohgushi | |
| 6,994,728 B2 | 2/2006 | Zubok et al. | |
| 6,994,729 B2 | 2/2006 | Zubok et al. | |
| 6,997,954 B2 | 2/2006 | Zubok et al. | |
| 6,997,955 B2 | 2/2006 | Zubok et al. | |
| 7,051,417 B2 | 5/2006 | Michelson | |
| 7,066,961 B2 | 6/2006 | Michelson | |
| RE39,196 E | 7/2006 | Ying et al. | |
| 7,105,030 B2 | 9/2006 | Despres, III et al. | |
| 7,115,143 B1 | 10/2006 | Michelson | |
| 7,166,129 B2 | 1/2007 | Michelson | |
| 2002/0062154 A1 | 5/2002 | Ayers | |
| 2002/0111680 A1 | 8/2002 | Michelson | |
| 2002/0143403 A1 | 10/2002 | Vaidyanathan et al. | |
| 2002/0161438 A1* | 10/2002 | Scott et al. | 623/11.11 |
| 2003/0050709 A1 | 3/2003 | Noth et al. | |
| 2003/0144664 A1 | 7/2003 | Cavagna | |
| 2003/0153984 A1 | 8/2003 | Khandkar et al. | |
| 2003/0233146 A1 | 12/2003 | Grinberg et al. | |
| 2004/0024462 A1 | 2/2004 | Ferree et al. | |
| 2004/0133281 A1 | 7/2004 | Khandkar et al. | |
| 2004/0143332 A1 | 7/2004 | Krueger et al. | |
| 2004/0172135 A1 | 9/2004 | Mitchell | |
| 2004/0176772 A1 | 9/2004 | Zubok et al. | |
| 2004/0176845 A1 | 9/2004 | Zubok et al. | |
| 2004/0220679 A1 | 11/2004 | Diaz et al. | |
| 2004/0225365 A1 | 11/2004 | Eisermann et al. | |
| 2004/0243126 A1 | 12/2004 | Carbone et al. | |
| 2004/0243241 A1 | 12/2004 | Istephanous et al. | |
| 2005/0033442 A1 | 2/2005 | Fisher et al. | |
| 2005/0055098 A1 | 3/2005 | Zdeblick et al. | |
| 2005/0060040 A1 | 3/2005 | Auxepaules et al. | |

| | | | |
|---|---|---|---|
| 2005/0079200 | A1 | 4/2005 | Rathenow et al. |
| 2005/0107888 | A1 | 5/2005 | Khandkar et al. |
| 2005/0177238 | A1 | 8/2005 | Khandkar et al. |
| 2005/0177240 | A1 | 8/2005 | Blain |
| 2005/0216092 | A1 | 9/2005 | Marik et al. |
| 2005/0228382 | A1 | 10/2005 | Richelsoph et al. |
| 2005/0273176 | A1 | 12/2005 | Ely et al. |
| 2006/0052875 | A1 | 3/2006 | Bernero et al. |
| 2006/0142862 | A1 | 6/2006 | Diaz et al. |

FOREIGN PATENT DOCUMENTS

| | | |
|---|---|---|
| WO | WO 99/47471 | 9/1999 |
| WO | WO 99/60956 | 12/1999 |
| WO | WO 01/17464 | 3/2001 |
| WO | WO 03/003950 A1 | 7/2002 |
| WO | WO 2004/019828 | 3/2004 |
| WO | WO 2004/026186 | 4/2004 |
| WO | WO 2004/054479 | 7/2004 |

OTHER PUBLICATIONS

International Search Report for PCT/US2002/018572, Dec. 16, 2002, 3 pages.
International Search Report for PCT/US2006/019254, Mar. 19, 2007, 1 page.
Written Opinion for PCT/US2006/019254, Mar. 19, 2007, 3 pages.
International Preliminary Report on Patentability for PCT/US2006/019254, Nov. 30, 2007, 1 page.
International Search Report for PCT/US06/31379, May 3, 2007, 1 pg.
International Search Report for PCT/US2003/040086, Jul. 16, 2004, 1 page.
International Search Report for PCT/US2007/061972, Nov. 14, 2007, 1 page.

* cited by examiner

POLYMER-CERAMIC ARTICULATION

This application claims the benefit of U.S. Provisional Application 60/298,669, filed Jun. 14, 2001. In addition, this application is a continuation-in-part of U.S. Ser. No. 10/171,376, filed Jun. 13, 2002, now U.S. Pat. No. 6,881,229.

BACKGROUND OF THE INVENTION

This invention relates generally to improvements in articulating joint prostheses, particularly such as an improved prosthetic hip joint or the like. More specifically, this invention relates to a combination of an improved ceramic material articulating against a well known and established metal for use in a metal-ceramic composite articulation which exhibits long wear characteristics with substantial elimination of wear debris, and which further exhibits reduced in-vivo fracture risk. Additionally, this invention is also related to the ability to use metal femoral heads with ceramic acetabular liners. The specific clinical benefits of this feature stem from the ability to use fracture resistant heads with low wear and substantial wear debris elimination, the use of large head diameters, which greatly facilitates minimizing risk of dislocation of the head from the prosthetic joint, and providing surgeons and patients with the choice of using this combination for revision of failed joint prostheses.

Typical articulating joints, which consist of a metal surface articulating with a ultra-high molecular weight polyethylene (PE) are inadequate. Clinical studies have shown that the principal cause of implant failure is osteolysis secondary to wear of the implant bearing-surfaces. The primary cause appears to be particulate debris in the form of ultra-high molecular weight polyethylene (PE) released, for example, from the PE acetabular liner bearing of a hip prosthesis[1]. Such PE wear debris when released into the peri-implant tissues appears to elicit a deleterious biologic reaction, incorporating foreign-body giant cell and macrophage cell responses leading to bone resorption, and eventual loosening of the prosthetic implant. As a consequence, alternative rigid-on-rigid bearing materials such as ceramic-on-ceramic (C—C) (such as alumina), metal-on-metal (M-M), and the recent cobalt chrome alloy (CoCr)—heavily cross linked PE (XPE) are being introduced.

Clinical experience from 1983 to the present has encompassed over two million alumina ceramic femoral-head implants.[2,3] Total hip replacement studies incorporating both CoCr and alumina ceramic heads have established the superiority of ceramic-PE couples over metal-PE couples, with alumina-alumina couples demonstrating 2-3 orders lower wear volume than the best ceramic-PE couples.[4] Even so, the major limitation to use of alumina ceramics today is the likelihood of brittle fracture, even in just a low incidence of 2% or less. From the limited series of clinical studies available in the United States, the failure incidence of alumina heads was found to be surprisingly high and of quite short follow-up periods, anywhere from 9 months to 10 years.[6,5] Thus the fracture incidence in ceramics is still of clinical concern. Typical ceramic materials have low toughness and are prone to failure by brittle fracture. As history has indicated, there is an urgent need to find an improvement to alumina, particularly with ceramic-ceramic couples which have higher bearing contact stresses.[6]

Low wear of articulating components occurs when the mating surfaces have comparable and high hardness, good surface finish, conformal surface geometry, compatible mechanical properties and a low coefficient of friction. It is because of the first three conditions that ceramic-ceramic couples have demonstrated very low wear. Contact damage results in the weaker material when the moduli and hardness of the articulating surfaces are very different, as is the case for CoCr-PE or even zirconia or alumina ceramic-PE. An ideal articulating low wear couple will have closely matching properties and high toughness. Traditional ceramics such as alumina are prone to brittle fracture owing to their low toughness. Such brittle failure in ceramic materials results from propagation of microcracks initiated at and just below the surface. Other ceramic materials such as zirconia, zirconia toughened alumina or $Si_3N_4$ that have higher toughness have significantly higher reliability than alumina, owing to the ability to avoid catastrophic failure. Specifically, using such ceramics can allow significant improvements in wear properties along with improved reliability. The specific advantages can be illustrated by considering the articulating hip joint. If the articulating hip joint can be made with a metal femoral head and a ceramic acetabular cup, additional significant clinical benefits can be obtained as listed below:

The metal femoral head does not fail catastrophically as ceramic heads can, assuring patient safety;

The metal head can be made of a larger size, up to 44 mm diameter, than ceramic heads can typically be made, providing the surgeon greater flexibility in implant size selection; and The metal head can be used as both a primary hip prosthesis or a revision hip prosthesis.

This invention describes a $Si_3N_4$ acetabular cup-CoCr femoral head couple. This couple is superior to other ceramic-metal couples such as alumina-metal,[7,8,9] owing to compatible properties such as hardness, tensile strength, elastic modulus, high fracture toughness, and lubricity. $Si_3N_4$ also has an optimal combination of toughness and strength properties that gives superior damage resistance: the ability to retain strength following contact damage. Friction property studies of $Si_3N_4$ ceramics show that $Si_3N_4$-(M-50) steel hybrid bearings and $Si_3N_4$—$Si_3N_4$ bearings had the lowest friction coefficients under both lubricated and dry conditions of the materials tested. In contrast, alumina ceramic-ceramic and alumina-steel bearings had approximately three times the friction coefficient when tested under similar conditions.

It is therefore an object of this invention to provide a new set of bio-compatible articulating surface materials for use in prosthetic joints which will have:

Ultra-low wear with volumetric wear rates of less than 1 $mm^3$/10 million cycles;

Long in-vivo life;

Wide range of sizes maximizing surgeon choice and optimizing fit to patient anatomy;

Wide bio-mechanical margin of safety for all sizes, minimizing risk of in-vivo fracture;

Preserving modularity of prosthetic articulating joint designs; and

Allowing both primary and revision prosthetic articulating joint designs.

SUMMARY OF THE INVENTION

In accordance with the invention, an improved joint prosthesis such as a hip, knee or shoulder joint or the like is provided with articulation between a first component and a second component, wherein at least one of these joint components is formed from a selected ceramic material designed for high fracture toughness or resistance, and further wherein the assembled joint components are designed for long-term articulation with minimal wear and resultant minimal production of undesired wear debris. The first component has an articulation surface formed from a bio-compatible ceramic with enhanced flexural strength and toughness properties, and wear properties compatible with the second component which has an articulation surface formed from a bio-compatible ceramic with enhanced flexural strength and toughness properties, or from a metallic alloy.

In a preferred form, the first component of the articulatory prosthesis is formed from a silicon nitride ceramic material doped with other oxides such as yttrium oxide and alumina. Other dopants can include magnesium oxide, or strontium oxide.

Other features and advantages of the invention will become more apparent from the following detailed description taken in conjunction with the accompanying drawings which illustrate, by way of example, the principles of the invention.

BRIEF DESCRIPTION OF THE DRAWINGS

The accompanying drawings illustrate the invention. In such drawings.

DETAILED DESCRIPTION OF THE PREFERRED EMBODIMENTS

Figure 1:
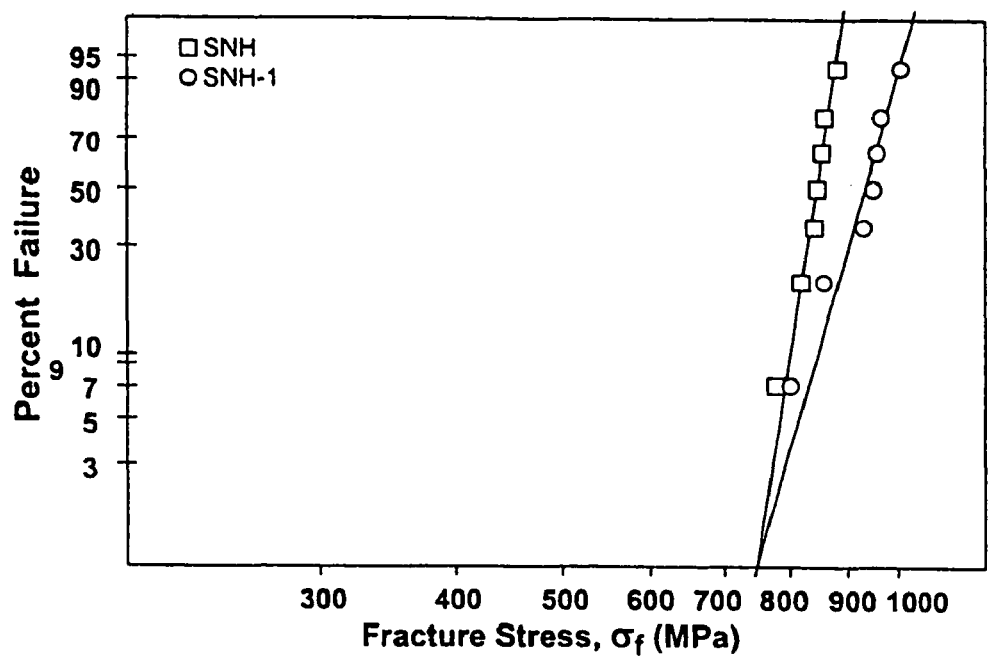
FIG. 1 is a graph illustrating the results of three point bend testing for $Si_3N_4$ ceramic test samples.

A ceramic-metal composite articulation is provided with substantial elimination of wear debris, wherein a ceramic material is provided with superior mechanical properties tailored for articulating with ceramic articulations having high flexural strength (greater than about 700 MPa), high fracture toughness (greater than about 7 $MPam^{1/2}$) and a high Weibull modulus (greater than about 20), in comparison with presently available bio-ceramics such as alumina or zirconia. The mechanical property enhancement enables ceramic materials with greater reliability and significantly reduced in-vivo fracture risk to be obtained. Preliminary in-vitro wear performance, to several million cycles using established test protocols, of head/cup components in a prosthetic hip joint made from these ceramics also demonstrates the ultra low wear characteristics. These material properties substantially eliminate polyethylene (PE) wear debris mediated implant failures by offering an optimal combination of bio-mechanical safety and reliability with ultra low wear performance.

Powders of $Si_3N_4$ and dopants such as alumina, yttria, magnesium oxide, and strontium oxide were conventionally processed to form a doped composition of silicon nitride. The dopant amount was optimized to achieve the highest density and mechanical properties. The homogeneous powders were then cold isostatic pressed at 300 Mega-Pascal (MPa) followed by sintering in a controlled atmosphere. Some cold isostatically pressed bars were hot isostatically pressed. A sintering temperature of 1875° C. was found optimal to achieve high density, absence of pores and other flaws and a uniform fine-grained microstructure. The best combination of density and mechanical properties was achieved with $Si_3N_4$ doped with 6 weight % $Y_2O_3$+4 weight % $Al_2O_3$.

Flexural strength was measured on standard 3-point bend specimens per American Society for Testing of Metals (ASTM) protocol method C-1161 and fracture toughness measured using single edge notched beam specimens per ASTM protocol method E399. Bend tests were conducted using test fixtures designed to minimize spurious stresses, with a nominal span of 40 mm. The bending load was applied using a universal testing machine at a cross-head displacement speed of 0.5 mm/min. At least 6 bars were tested to get a measure of the distributions and the Weibull modulus. The composition/process that gave the highest fracture toughness, Weibull modulus and damage resistance was selected for fabricating 28 mm hip prosthesis implant articular femoral head and acetabular cup components. 28 mm CoCr metal femoral heads were obtained from Biomet, Inc. of Warsaw, Ind.

Wear performance tests of up to 1 million cycle duration were conducted. Wear detection was primarily done gravimetrically with some inspection of the surfaces for wear track analysis and wear debris analysis using scanning electron microscopy. In the hip prosthesis simulator test, the rotating cams (unidirectional) carrying the specimen chambers were driven at 1 Hz frequency through +23° arcs on orthogonal axes. Each vertical load column had a self alignment device and friction torque sensors. In addition, both the anti-rotation peg and the friction sensor pegs were guide mounted on rollers to provide continuous constraint. For this study, the cam rotation was synchronized with the hip-joint loading. The "Paul" physiologic load profile was used.[10,11] All tests were run at 2 KiloNewton (kN) peak load/0.2 kN minimum load. The test cups were arranged in an anatomically inverted position in the hip prosthesis simulator. A solution of 90% bovine serum was used as the lubricant with 10% standard additives of sodium azide and ethylene diamine tetra-acetic acid (EDTA). The specimen chambers were replenished with distilled water during the tests. Lubricant temperature was monitored but not controlled since the lubricant's bulk temperatures run in the range 36-40° C., close to body temperature. The ceramic cups were not sterilized prior to test. Soak control cups were not used for the ceramic-ceramic and ceramic-metal wear tests. The diametral clearance, surface finish and sphericity tolerance was noted. Component wear was determined using a gravimetric method. Wear components were cleaned and dehydrated and each set weighed four times in order with a 32 mm CoCr head as a calibration standard. The overall volumetric wear rate was determined by the slope of the linear regression line. A consistent wear rate, i.e. gradient of the linear regression trend was deemed more significant than the actual magnitude of the wear at any point in time.

Microstructural features such as grain size, pore size, porosity and defects were observed on sintered $Si_3N_4$ specimens after etching with carbon tetra-fluoride plasma. The specimens were found to be dense, with no detectable porosity, and had substantially uniform grain size consistent with high quality ceramics.

Figure 2:
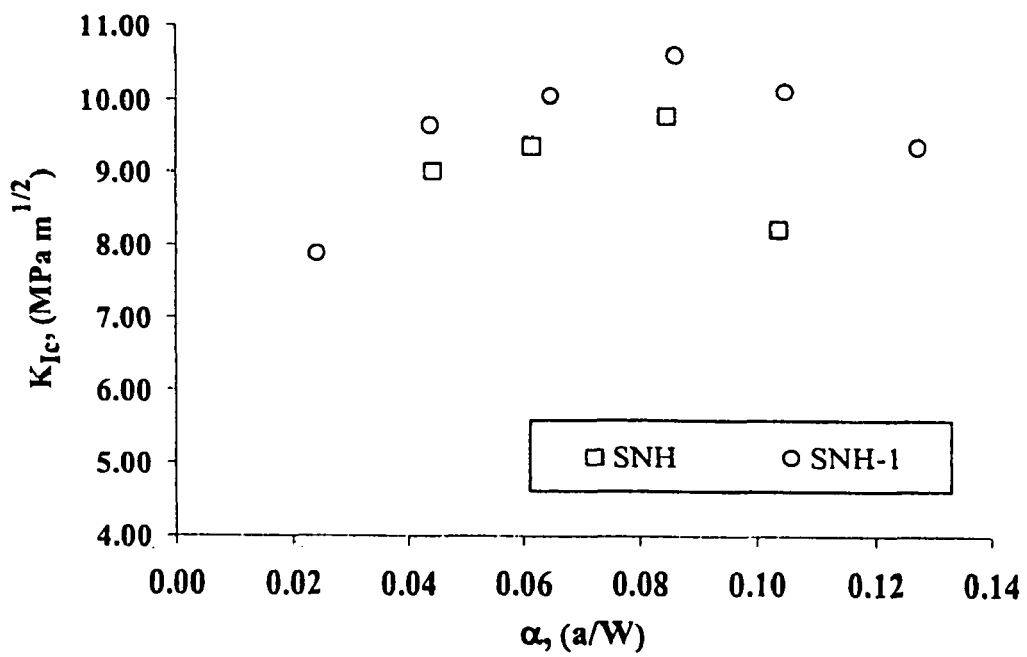
FIG. 2 is a graph illustrating the fracture toughness of the $Si_3N_4$ ceramic test samples depicted in FIG. 1.

For fracture toughness testing, 2.5 mm×5 mm×25 mm bar specimens with varying notch depth, a, were prepared. The prepared specimens were tested in three-point bending with a span length of 20 mm. The resultant fracture loads were converted to fracture toughness values using ASTM protocol method E399. The fracture strength and toughness values are given in Table 1, and are plotted in FIGS. 1 and 2. As expected, hot iso-statically pressed specimens labeled as SNH and SNH-1 exhibited high strength, toughness and Weibull moduli. Hence hot iso-static pressed components were fabricated into acetabular and femoral components. The relevant mechanical characterization data obtained are tabulated in Table 1.

TABLE 1

Weibull Modulus and Characteristic Fracture Strength of $Si_3N_4$.

| Material | Weibull Modulus M | Characteristic Strength $\sigma_f$ (MPa) | Fracture Toughness $K_{Ic}$ (MPa$m^{0.5}$) |
|---|---|---|---|
| SNH | 34.9 | 853 | 9.10 (0.66) |
| SNH-1 | 19.1 | 952 | 9.61 (0.95) |

The results indicate that SNH and SNH-1 have a substantially optimized high flexural strength, greater than about 900 MPa, and fracture toughness, greater than about 9 MPa$m^{0.5}$.

A trial wear test using a hip simulator was conducted using $Si_3N_4$ acetabular cups articulating against Biomet's standard 28 mm CoCr metal femoral heads (previously identified). Three Biomet 28 mm heads were used. The mating $Si_3N_4$ acetabular ceramic cups were ground without lapping. The surface roughness value ($R_a$) value was ~0.5 µm. High wear of the metal femoral heads was observed, attributed to the higher surface roughness, which resulted in scouring the surface of the CoCr metal femoral heads. The wear behavior was found to be linear and typical of 3-body wear, dominated by unstable characteristics. The lubricant solution exhibited the concomitant amount of CoCr metal debris. Further, the wear tracks showed non-polar contact rather than polar contact as anticipated from the low diametral clearance. Fine scratch marks and wear tracks were observed midway between the pole and equator, while the pole had a shiny sheen, indicative of equatorial contact.

For subsequent wear tests, the $Si_3N_4$ acetabular and femoral components were ground and lapped to obtain an $R_a$<0.05 µm. The diametral clearance and sphericity was also varied. The CoCr metal femoral heads were made from a wrought high carbon CoCr alloy containing about 64 weight % cobalt, about 28% weight chromium, about 6% weight molybdenum, about 0.5% weight manganese, about 0.25% weight iron, about 0.2% weight nickel, about 0.2% weight nitrogen and about 0.23% weight carbon. The conventional low carbon CoCr alloy had a similar elemental weight composition with a carbon content of about 0.06% by weight. Such CoCr alloys used for joint prostheses are wrought alloys conforming to ASTM Specification 1537. This high carbon alloy had an elastic modulus greater than 210 giga Pascal (GPa), which had a closer modulus match to the doped $Si_3N_4$ ceramic (elastic modulus ~300 GPa) compared to the low carbon CoCr alloy used in the trial run. The Vickers hardness of these alloys is in the range of 4-5 GPa compared to between 14-16 GPa $Si_3N_4$. The elastic modulus and hardness of the articulating surfaces of the doped $Si_3N_4$ ceramic-$Si_3N_4$ ceramic or the doped $Si_3N_4$ ceramic-CoCr alloy pair are better matched compared to either CoCr-PE, or CoCr-XPE articulations. This was expected to result in better wear performance.

Relevant design data pertaining to the articulating femoral head and acetabular cup pairs chosen for the wear study are tabulated in Table 2. Stations 1 and 2 had $Si_3N_4$ ceramic acetabular cup-$Si_3N_4$ ceramic femoral head bearings, and Station 3 had a $Si_3N_4$ ceramic acetabular cup-CoCr metal femoral head bearing. For the $Si_3N_4$ ceramic-$Si_3N_4$ ceramic bearings in Stations 1 and 2, a 70 and 100 µm diametral clearance was chosen to test the effect of run-in wear. The sphericity tolerance of the ceramic acetabular cups was between 1-1.5 µm in all cases and was less than 0.5 µm for both the ceramic femoral heads. For the $Si_3N_4$ acetabular cup-CoCr femoral head bearing, a diametral clearance of about 200 µm was selected.

TABLE 2

Design Tolerances for the Second Wear Performance Test.

| | Components | Diameter (mm) | Surface Roughness, Ra (µm) | Sphericity (µm) |
|---|---|---|---|---|
| Station 1 | Ceramic Cup | 28.0734 | 0.0390 | 1.486 |
| | Ceramic Head #4 | 27.9704 | 0.0440 | 0.419 |
| | Diametral Clearance | 103 µm | | |
| Station 2 | Ceramic Cup | 28.0552 | 0.0074 | 1.448 |
| | Ceramic Head #2 | 27.9856 | 0.0447 | 0.851 |
| | Diametral Clearance | 69.6 µm | | |
| Station 3 | Ceramic Cup | 28.0252 | 0.0091 | 1.041 |
| | CoCr Head 743650 C | 27.7986 | 0.0149 | 3.785 |
| | Diametral Clearance | 226.6 µm | | |

Figure 3:
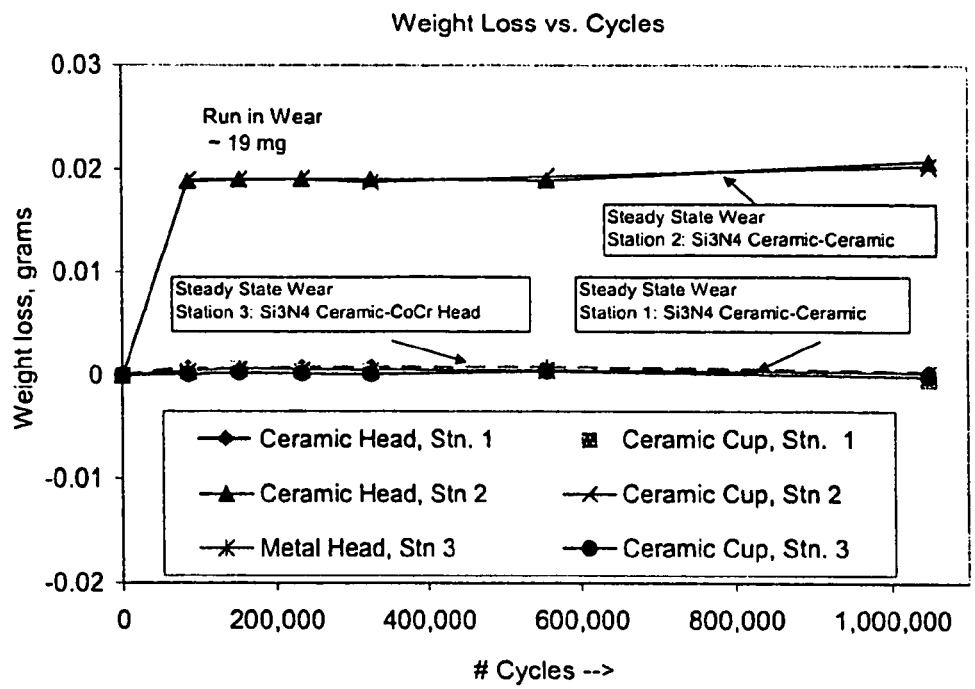
FIG. 3 is a graph showing wear test results for simulated hip prostheses using $Si_3N_4$ ceramic acetabular cup and femoral heads ($Si_3N_4$ ceramic-$Si_3N_4$ ceramic, Stations 1 and 2), and a $Si_3N_4$ ceramic acetabular cup and CoCr metal femoral head ($Si_3N_4$ ceramic-metal, Station 3)

The results from the wear test are plotted in FIG. 3. Stations 1 and 3 with diametral clearance of about 100 and 225 µm showed ultra low wear, with no observable run-in wear. In contrast, Station 2 with a low diametral clearance of about 70 µm showed classic biphasic behavior as is typical for metal-metal and ceramic-ceramic bearings. This biphasic behavior is attributed to the lower diametral clearance which, owing to inadequate film lubrication between the articulating surfaces, results in run-in wear.

Comparing the wear performance of the silicon nitride ceramic-ceramic bearings in Stations 1 and 2, it was noted that the bearing in Station 2 exhibited a "grinding" noise along with an increase in lubricant temperature during the run-in period. Following the run-in period, both Stations 1 and 2 behaved normally, with very low steady state wear rates. This was attributed to the lower diametral clearance used in Station 2, which may have resulted in an inadequate lubricant film to be developed between the femoral head and acetabular cup. The wear performance of the $Si_3N_4$ acetabular ceramic cup-CoCr metal femoral head bearing was characterized by an absence of run-in wear, similar to that of Station 1, and very low steady state wear rates. This result was as anticipated where, with better modulus matching, a ceramic-metal articulation couple could provide a ultra-low wear alternative for total hip arthroplasty.

Figure 4:
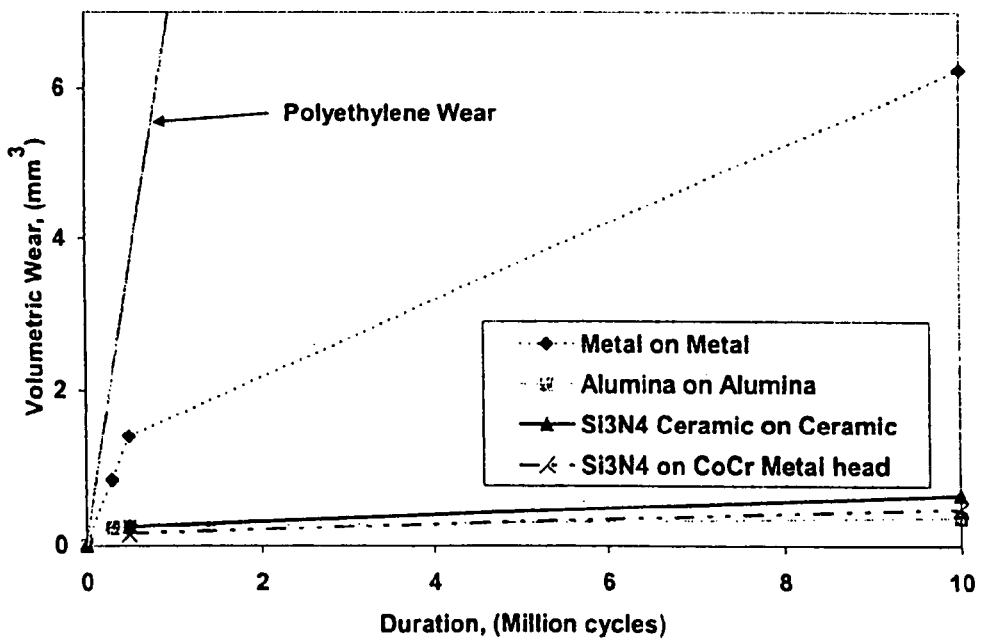
FIG. 4 is a graph showing wear performance of $Si_3N_4$ ceramic acetabular cup and ceramic femoral head components ($Si_3N_4$ ceramic-$Si_3N_4$ ceramic), and $Si_3N_4$ ceramic cup and metal ($Si_3N_4$ ceramic-metal) head hip prostheses through an extended wear cycle, in comparison with metal-to-metal and traditional ceramic-to-ceramic in-vitro wear data.

The wear performance of these bearings was obtained over a 4 million cycle period. The weight loss data obtained were converted to volumetric wear rates and extrapolated to 10 million cycles to enable a comparison to literature values. The data, plotted in FIG. 4, indicate that the $Si_3N_4$ femoral head-$Si_3N_4$ acetabular cup bearings and the $Si_3N_4$ acetabular cup-CoCr metal femoral head show ultra-low wear of 0.65 mm$^3$/10 million cycles and 3.4 mm$^3$/10 million cycles respectively. In comparison, wear rates of 62 mm$^3$/10 million cycles for CoCr-PE (clinical data), 6.5 mm$^3$/10 million cycles for metal-metal (in-vitro) wear and 0.35-0.6 mm$^3$/10 million cycles for alumina ceramic-alumina ceramic (in-vitro) have been reported.

Observation of the articulating components after 1 million cycles of wear testing, validated the ultra-low wear behavior by exhibiting a complete absence of wear tracks or other wear patterns. The articulating surfaces retained their high shine, consistent with the negligible weight loss observed for the components.

The above-described optimized material properties of $Si_3N_4$ have demonstrated a 100% increase of fracture toughness over alumina, and a 50% increase in fracture strength over alumina ceramics, which typically have a fracture toughness of about 5 $MPam^{0.5}$ and a flexural strength of about 600 MPa. These properties of $Si_3N_4$ can allow the manufacture of total hip arthroplasty implants and other prosthetic joint implants such as knee and shoulder joints with significantly higher safety and reliability. Wear performance of $Si_3N_4$ femoral head-$Si_3N_4$ acetabular cup components and $Si_3N_4$ acetabular cup-CoCr femoral head components indicates that these bearings are better than metal-metal bearings and comparable to ceramic-ceramic bearings, with a volumetric wear rate of 2 orders of magnitude lower than CoCr-PE and 20 times lower than CoCr-XPE bearings.

The combination of the metal femoral head and a ceramic acetabular cup described above offers unprecedented benefits owing to inherent fracture resistance and excellent wear performance. The fracture resistance is derived from the use of metal femoral heads instead of ceramic femoral heads. It is well known from finite element analyses of the stresses in hip prosthetic joints that the femoral head component is subjected to high tensile stresses. Historically, such tensile stresses have been implicated in ceramic head fracture. Metal femoral heads do not fracture owing to the ductile nature of metals. Hence use of metal heads avoids fracture risk. In contrast, the acetabular cup component is typically subjected mainly to compressive stresses, which ceramics are designed to withstand. Furthermore, the combination of high toughness and flexural strength provides improved capability to withstand loads. Thus, as a general design principle for articulating prosthetic joints, the articulating component subjected to the higher tensile stresses can be made from a metal and the mating articulating component subjected to the higher compressive stresses can be made from the high strength high toughness ceramic with favorable tribiological properties. To illustrate this by way of example, in the hip joint, the femoral head can be made of metal and the mating acetabular cup can be made of the ceramic. In the case of knee joints, the condylar component which is subjected to higher tensile stresses, can be made from metal while the mating tibial component can be made from the ceramic. Similarly, the concept can be extended to other articulating prosthetic joints such as the shoulder joint.

The use of $Si_3N_4$ femoral head-$Si_3N_4$ acetabular cup components and $Si_3N_4$ acetabular cup-CoCr femoral head components in the instant invention to demonstrate the concept of using a fracture resistant metal alloy articulating with optimized ceramics to obtain an ultra low wear joint are illustrative of the general concept. Alternate metal alloys suitable for medical implants such as zirconium based alloys, titanium based alloys or stainless steel alloys may be used for the femoral head of a hip joint (or the component subjected to higher tensile stresses). Alternate enhanced toughness ceramic materials such as doped zirconia or zirconia toughened alumina could also be used for the acetabular component of a hip joint (or the component subjected to higher compressive stresses). This concept can also be applied to other orthopedic joints such as the shoulder or knee joint.

In accordance with further alternative forms of the invention, the improved ceramic material having high flexural strength and high toughness properties as described herein, may also be used in an implantable articulating bone or joint prosthesis for articulation against a mated articulation surface defined by a thermoset or thermoplastic polymer which may incorporate fiber or non-fiber reinforcing materials, or defined by a naturally occurring structure such as natural patient bone.

More particularly, conventional articulating implants such as hip or knee implants have been constructed from Co—Cr alloys for the convex bearing surface (e.g. the femoral head for hip implants or the condyle for knee implants) and softer polymeric materials for a mating bearing surface such as the acetabular liner for the hip implant or a tibial insert for the knee implant. Such prior art bearing materials eventually conform to each other's shape to provide an optimal fit, whereby wear is minimized, resulting in longer-lasting prosthetic devices. An example of the softer polymeric material is ultra-high molecular weight polyethylene (UHMWPE).

The instant invention described herein can also be used to construct a ceramic-on-polymer implant. One advantage of such an implant is the absence of metal ion debris, which may be potentially harmful in the long term. Metal ion debris is attacked by body fluids causing the body to ultimately expel the debris systemically. This in turn results in extremely high metal ion concentrations in the body with potentially toxic effects to the patient. Additionally, in the presence of third-body wear such as might result from cement particles or bone debris being present in between the metal and polymer components, the wear process is accelerated with the polymeric component being worn away at a faster rate due to the scratching of the metal component. Ceramic bearing components, being more scratch resistant, and having lower friction against polymers such as ultra high molecular weight polyethylene (UHMWPE), afford a reduction in these deleterious effects and promotes implant longevity. Furthermore, the superior mechanical properties of the ceramic material of the present invention avoid a major drawback of traditional bioceramics having a lower threshold of mechanical failure.

The recent introduction of cross linked polyethylene (XLPE) as an alternative polymer bearing surface in articulating implants was another attempt to address the problem of high wear of UHMWPE implant bearing components. However, XLPE polymers have a lower fracture toughness than UHMWPE and in the presence of third body wear particles, remain susceptible to high wear against metal bearing components. However, the above mentioned advantages of using a ceramic on polymer implants also apply to ceramic on XLPE implants.

Thus, the invention of a unique ceramic material disclosed herein, having high flexural strength and high toughness properties, articulating with UHMWPE or XLPE affords the high wear resistance and low friction advantages of ceramic-on-polymer bearings while avoiding their disadvantages. The invention is thus also directed to constructing an articulating implant of the ceramic-on-XLPE or ceramic-on-UHMWPE, which represents a unique subset of ceramic-on-polymer bearing implants, exhibiting even longer overall useful life relative to conventional implants utilizing metal or conventional ceramic-on-UHMWPE or XLPE.

In accordance with a further aspect of the invention, the improved ceramic material having high flexural strength and high toughness properties as described herein may also be used for articulating against a naturally occurring structure such as patient bone. By way of illustrative example, in some instances, a significant number of hip patients require hemi-arthroplasty, in which case only one half of the typically two component articulating hip joint bearing structure is replaced. In such hemi hip arthroplasty, a ball shaped head may be used to resurface the patient's defective or diseased femoral head. Alternatively, the ball head may consist of a femoral head attached to a stem, which is inserted into the femoral medullary canal anchoring the implant to the patient's femur. The prosthetic head articulates with the patient's otherwise healthy and naturally occurring bone structure defined by the acetabular socket in a similar fashion to the original hip joint, restoring a substantial or at least partial range of linear and rotational motion. Thus in hemi-arthroplasty the implant component must match the contours of the natural articulation surface on the anatomic bone structure, and must be conducive to low friction and wear of the natural segment. The present invention is also directed to such hemi-arthroplasty implants where the improved ceramic bearing material is contoured to fir the patient's natural counter bearing surface, such as a ceramic ball structure for articulating against the patient's acetabular socket in the case of hemi-hip arthroplasty. Persons skilled in the art will recognize that this concept may be employed in other anatomical joint structures.

A variety of further modifications and improvements in and to the invention will be apparent to those persons skilled in the art. Accordingly, no limitation on the invention is intended by way of the foregoing description and accompanying drawings, except as set forth in the appended claims.

LITERATURE CITED

[1] Callaway G. H, Flynn W., Ranawat C. S., and Sculco T. P., J. Arthroplasty, 10, No. 6:855-859,1995.
[2] Willman G., Pfaff H. G., and Richter H. G., Sonder. aus BioMed. Technik, 40, 12, pp. 342-346, 1995.
[3] Clarke I. C. and Gustafson A., 6$^{th}$ Biomat. Symp. Implant Matis. In Orthop. Surg., ed. H. Willert and G. Buchorn, Gottingen University, Germany, in press, 1995.
[4] Clarke I. C. and Gustafson A., In Press, Intl. Ceramics Congress, Otsu City, Japan, November 1997.
[5] Mangione, P. Pascarel, X., Vinciguerra B, and Honton J. L., Intl, Orthop., 18, pp. 359-362, 1994.
[6] Holmer P. and Nielsen P. T., J. Arthrop., 8, 567, 1993.
[7] B. Bhushan and L. B. Sibley, "Silicon Nitride Rolling Bearings for Extreme Operating Conditions", ASME Trans. 25, 4, pp. 417-428, 1981.
[8] D. L. Allen, "Effect of Composition and Physical Properties of Silicon Nitride on Rolling Wear and Fatigue Performance", Tribology trans., Vol. 37, 2, pp. 410-414, 1994.
[9] J. W. Lucek, "Rolling Wear of Silicon Nitride Bearing Materials", ASME Gas Turbine and Aeroengine Congress and Expo., Brussels, Belgium, 1990.
[10] Clarke I C, McKellop H A, Okuda R, McGuire P, Young R, and Hull D, "Materials and prosthesis design criteria—hip simulator studies", Trans. 28th Ann. ORS, New Orleans, pp. 292, 1982.
[11] McKellop H and Clarke I. C., "Degradation and wear of Ultra-High Molecular-Weight Polyethylene" In American Society for Testing & Materials, ASTM STP 859:351-368, 1985.

What is claimed is:

1. An implantable articulating bone prosthesis, comprising:
   a first component having an articulation surface formed from a biocompatible doped silicon nitride ceramic having a flexural strength greater than about 700 Mega-Pascal (MPa) and a toughness greater than about 7 Mega-Pascal root meter (MPam$^{0.5}$), wherein said doped silicon nitride comprises one or more dopants selected from the group consisting of yttrium oxide, magnesium oxide, strontium oxide, and alumina; and
   a second component having an articulation surface formed from a biocompatible polymer which is not a ceramic, wherein said first component and said second component are shaped for a joint prosthesis and one of said articulation surfaces of said first component and said second component has a generally concave shape and the other of said articulation surfaces of said first component and said second component has a generally convex shape.

2. The implantable articulating bone prosthesis of claim 1 wherein said biocompatible doped silicon nitride ceramic comprises dopants including yttrium oxide and alumina.

3. The implantable articulating bone prosthesis of claim 1 wherein said biocompatible polymer comprises one or more fiber reinforced or non-fiber reinforced biocompatible materials selected from the group consisting of thermoset polymers and thermoplastic polymers.

4. The implantable articulating bone prosthesis of claim 1 wherein the biocompatible polymer comprises ultra high molecular weight polyethylene (UHMWPE).

5. The implantable articulating bone prosthesis of claim 1 wherein the biocompatible polymer comprises cross linked polyethylene (XLPE).

6. The implantable articulating bone prosthesis of claim 1 wherein said first component and said second component are shaped for a hip joint prosthesis.

7. The implantable articulating bone prosthesis of claim 1 wherein said first component and said second component are shaped for a knee joint prosthesis.

8. The implantable articulating bone prosthesis of claim 1 wherein said first component and said second component are shaped for a shoulder joint prosthesis.

\* \* \* \* \*